United States Patent
Szabo et al.

(10) Patent No.: US 9,869,624 B2
(45) Date of Patent: Jan. 16, 2018

(54) METHOD AND APPARATUS FOR CHARACTERIZING INTERFACIAL TENSION BETWEEN TWO IMMISCIBLE OR PARTIALLY MISCIBLE FLUIDS

(71) Applicant: Schlumberger Technology Corporation, Sugar Land, TX (US)

(72) Inventors: Geza Horvath Szabo, Sugar Land, TX (US); John Ratulowski, Edmonton (CA); Dmitry Eskin, Edmonton (CA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 717 days.

(21) Appl. No.: 14/357,573

(22) PCT Filed: Dec. 14, 2012

(86) PCT No.: PCT/US2012/069698
§ 371 (c)(1),
(2) Date: May 12, 2014

(87) PCT Pub. No.: WO2013/090690
PCT Pub. Date: Jun. 20, 2013

(65) Prior Publication Data
US 2014/0316722 A1 Oct. 23, 2014

Related U.S. Application Data

(60) Provisional application No. 61/576,037, filed on Dec. 15, 2011.

(51) Int. Cl.
*G01N 13/00* (2006.01)
*G01N 13/02* (2006.01)

(52) U.S. Cl.
CPC .............. *G01N 13/00* (2013.01); *G01N 13/02* (2013.01); *G01N 2013/0241* (2013.01)

(58) Field of Classification Search
CPC .............. G01N 13/00; G01F 1/42; G01F 1/44
(Continued)

(56) References Cited

U.S. PATENT DOCUMENTS 6,463,810 B1 * 10/2002 Liu ........................... G01F 1/44
73/861
7,266,995 B2 * 9/2007 Skogo ..................... G01N 13/02
73/64.48

(Continued)

OTHER PUBLICATIONS

M.S. Chandra, et al, "Impact of Pre-equilibration on the Assessment Methodology of Interfacial Tension Measured between Aqueous and Heavy Oil Phases," Energy & Fuels, 25(6), 2011, pp. 2542-2550.

A. Yeung, et al., "Micropipette: a new technique in emulsion research," Nov. 15, 2000, Colloids and Surfaces (A: Physicochemical and Engineering Aspects), vol. 174, pp. 169-181.

(Continued)

*Primary Examiner* — John Breene
*Assistant Examiner* — Kaleria Knox

(57) ABSTRACT

An apparatus (and method) for characterizing interfacial tension between a non-wetting phase fluid and a wetting phase fluid of a slug flow employs a capillary structure that is configured to contain a slug of the non-wetting phase fluid of the slug flow. The slug has a leading edge meniscus and a trailing edge meniscus, and the capillary structure has a venturi-like section. A pressure sensor is configured to measure differential pressure between first and second locations of the capillary structure. The first location is disposed upstream of the leading edge meniscus of the slug with the leading edge meniscus of the slug contained within the venturi-like section. The second location is disposed downstream of the trailing edge meniscus of the slug. Data processing means is configured to derive a measure of (Continued)

interfacial tension based upon the differential pressure measured by the pressure sensor and, optionally, geometry of the capillary structure.

28 Claims, 5 Drawing Sheets

(58) Field of Classification Search
USPC .................. 702/30, 47, 50; 73/861, 861.52
See application file for complete search history.

(56) References Cited

U.S. PATENT DOCUMENTS

| | | | |
|---|---|---|---|
| 7,434,479 B2* | 10/2008 | Gulich | G01F 1/42 73/861.52 |
| 2005/0116070 A1 | 6/2005 | Ganan et al. | |
| 2010/0305881 A1* | 12/2010 | Atkinson | G01F 1/44 702/47 |
| 2011/0106456 A1* | 5/2011 | Szabo | G01N 13/00 702/30 |

OTHER PUBLICATIONS

J.A. Pojman, et al., "Evidence for the Existence of an Effective Interfacial Tension between Miscible Fluids: Isobutyric Acid-Water and 1-Butanol-Water in a Spinning-Drop Tensiometer," Feb. 16, 2006, Langmuir, vol. 22, Issue 6, pp. 2569-2577.

A. Passerone, et al., "A New Experimental Method for the Measurement of the Interfacial Tension between Immiscible Fluids at Zero Bond Number," Oct. 1, 1991, Journal of Colloid and Interface Science, vol. 146, No. 1, pp. 152-162.

S. Lee, et al., "Equilibrium and Dynamic Interfacial Tension Measurements at Microscopic Interfaces Using a Micropipet Technique, 1. A New Method for Determination of Interfacial Tension," Langmuir 2001, 17(18), pp. 5537-5543.

Q. Ke, et al., "Fabrication of mechanically robust superhydrophobic surfaces based on silica micro-nanoparticles and polydimethylsiloxane," Surface and Coatings Technology 205 (21-22), pp. 4910-4914, 2011.

H. Gu, et al, "Interfacial tension measurements with microfluidic tapered channels," Colloids and Surfaces A: Physicochemical and Engineering Aspects, 389 (2011), pp. 38-42.

* cited by examiner

METHOD AND APPARATUS FOR CHARACTERIZING INTERFACIAL TENSION BETWEEN TWO IMMISCIBLE OR PARTIALLY MISCIBLE FLUIDS

BACKGROUND

Field

The present application relates to analysis of immiscible or partially miscible fluids. Specifically, the present application relates to measuring the interfacial tension between immiscible or partially miscible fluids.

Related Art

A fluid is a substance that continually deforms or flows under an applied shear stress. It may contain liquids, gases, and solids, and generally takes on the shape of the container in which it is housed.

An emulsion is a fluid that consists of a mixture of at least two fluid phases that are immiscible or partially miscible with respect to one another. In a two-phase emulsion, one fluid (the dispersed phase) is dispersed within the other (the continuous phase). The creation of an emulsion from separate phases typically requires stirring, shaking, or some other form of energy input. The process by which emulsions are created is called emulsification. In an emulsion, the degree and uniformity of dispersion of the dispersed phase within the continuous phase will generally depend on the nature of the fluid phases of the emulsion, the rate of mixing, and the length of time that the fluid phases are mixed. If the interfacial tension between the dispersed and continuous phases of an emulsion is low or the kinetic stability of the thin liquid films between the approaching emulsion droplets is low, then the emulsion could be unstable. Over time, the components of an unstable emulsion tend to separate if the mixing, stirring, or shaking is ceased. One common example of an emulsion that quickly separates is oil and vinegar salad dressing. When an oil and vinegar salad dressing bottle is shaken, the components of the salad dressing are temporarily dispersed. When the shaking ceases, the components separate.

Because the molecules at the surface of a liquid have potential energies greater than those of similar molecules in the interior of the liquid, an amount of work equal to this difference in potential energy must be expended to bring a molecule from the interior to the surface. Surface tension is proportional to this work. At the interface between the dispersed and continuous phases of an emulsion, the dissimilar molecules in the adjacent layers facing each other across the interface also have potential energies different from those in their respective phases. Each molecule at the interface has a potential energy greater than that of a similar molecule in the interior of its bulk phase by an amount equal to its interaction energy with the bulk phase across the interface. For most purposes, however, only interactions with adjacent molecules need to be taken into account. Because of the differences in potential energies for the molecules of the interface, work must be expended to form the interface. Interfacial tension is a measure of such work.

Interfacial tension is an important parameter in reservoir engineering calculations. For example, it is often used to determine capillary number in a reservoir. Capillary number is a dimensionless parameter that characterizes the ratio of viscous forces to interfacial tension forces. For a flowing liquid, if the capillary number is much greater than 1, then viscous forces dominate over interfacial forces; however if the capillary number is much less than 1, then viscous forces are negligible compared with interfacial forces. Interfacial tension is also used to derive capillary pressure and saturation profiles in a reservoir.

Interfacial tension is also a basic parameter that can be used to study the stability of emulsions, efficiency of cleaning and washing operations, and the properties of surfactants. A surfactant reduces the interfacial tension by adsorbing at the interface between the dispersed and continuous phases of the emulsion. In enhanced oil recovery applications, such as water flooding, steam flooding, or steam assisted gravity drainage (SAGD), high interfacial tension at the oil-water interface can prevent the migration of oil in the reservoir and thus hinder production. The surfactant is injected into the reservoir in conjunction with the water or steam in order to reduce the interfacial tension at the oil-water interface and thus improve the migration of oil in the reservoir and aid in production of the reservoir. When planning such enhanced oil recovery operations, a large number of surfactants are screened to characterize the interfacial tension at the temperature and pressure conditions of the reservoir.

Interfacial tension between the dispersed phase and the continuous phase of an emulsion can be measured with the interface in a state of full thermodynamic equilibrium. This is typically referred to as static interfacial tension. Full thermodynamic equilibrium requires thermodynamic equilibrium between the bulk of the phases of the emulsion and the interface, in addition to the usually understood equilibrium conditions for the bulk of the phases. The interface itself should also be in equilibrium, which means, among other things, that the lifetime of interface should approach infinity.

Interfacial tension between the dispersed phase and continuous phase of an emulsion can be measured with the interface not in a state of full thermodynamic equilibrium. This is typically referred to as dynamic interfacial tension. Measurements of dynamic interfacial tension can be made on non-equilibrated interfaces, which are generated by either interfacial area expansion or reduction. The interfacial area generation is more often used in practice. For this case, the new interface can be generated in a single step and the interfacial tension will be time dependent. It is also possible to generate new interfaces continuously. In this case, the interfacial tension will be location dependent. Generally, the dynamic interfacial tension is dependent on the lifetime of the interface studied and its value approaches the static interfacial tension asymptotically in time.

There are a number of known methodologies for measuring interfacial tension. For example the capillary rise, sessile drop, spinning drop, and maximum bubble pressure methodologies are often used and commercial instruments are usually available employing these specific methodologies. The densities of the phases are most often needed to measure the interfacial tension. For measuring dynamic interfacial tension, the densities of the phases can change significantly during the equilibration process. Using the densities for the phases assuming static conditions can lead to errors in measuring dynamic interfacial tension. See Mahavadi, C. S., Zacharia, J., and Horvath-Szabo, G., "The Impact of Pre-equilibration on the Assessment Methodology of Interfacial Tension Measured between Aqueous and Heavy Oil Phases," *Energy & Fuels*, 25(6), 2011, pp. 2542-2550.

In biology, the micropipette methodology is often used to measure the tension of cell membranes. This approach is based on capturing a single cell with a pipette having an orifice diameter smaller than the diameter of the cell. A small suction pressure is applied in the pipette to keep the cell at the top of the pipette for capturing. To measure the membrane tension, the suction pressure is smoothly increased until a portion of the cell is drawn into the capillary while the rest of the cell remains outside. At this stage, the suction pressure applied on the capillary is counterbalanced by the Laplace pressure differences of the curvatures of the two spherical segments of membrane, which are inside and outside of the capillary. Because the Laplace pressure is dependent on the radius of the curvature and the membrane tension, the membrane tension can be obtained by simple algebraic manipulations using the curvatures of the two spherical segments and the suction pressure.

The applicability of the micropipette methodology for oil-water systems was demonstrated by comparing the interfacial tension of different hydrocarbon/water systems measured by some traditional technique and the micropipette method. See Yeung, A., Dabros, T., Masliyah, J., and Czarnecki, J., "Micropipette: a new technique in emulsion research," *Colloids and Surfaces, A: Physicochemical and Engineering Aspects*, Volume 174, Issues 1-2, 15 Nov. 2000, pp. 169-181. For measuring the interfacial tension of a given hydrocarbon-water system, suction pressure was applied to a micropipette to capture a single emulsion droplet at the entrance to an interior capillary chamber of the micropipette. The interior capillary chamber was either hydrophobic (i.e., zero contact angle could be assumed for an oil phase droplet where oil-in-water emulsions were studied) or hydrophilic (i.e., zero contact angle could be assumed for an aqueous phase droplet where water-in-oil emulsions were studied). After capturing the droplet at the entrance to the interior capillary chamber, the suction pressure was gradually increased, which causes the radius of curvature of the oil-water interface within the interior capillary chamber to become smaller. There is a range of suction pressure within which the droplet stays attached at the entrance of the interior capillary chamber. When the radius of curvature of the interface situated inside the interior capillary chamber becomes equal to the internal radius of the interior capillary chamber, the suction pressure reaches its maximal or critical value, $p_{cr}$. When the pressure is increased beyond the critical value $p_{cr}$, the emulsion droplet is completely sucked into the interior capillary chamber. The methodology measured the interfacial tension ($\sigma$) of the given hydrocarbon-water system with the following formula:

$$\sigma = \frac{p_{cr} R_p}{2(1 - R_p/R_o)} \quad (1)$$

where $p_{cr}$ is the critical suction pressure, $R_p$ is the radius of the interior capillary chamber, and $R_o$ is the radius of the drop segment that lies outside the interior capillary chamber.

These radii were obtained from image analysis, while the suction pressure was measured by a sensor. The above-described methodology has some disadvantages. First, it requires human intervention for capturing the droplet. Second, it requires simultaneous usage of inverted microscopy, micromanipulators, and a suction pump to capture individual emulsion droplets. Third, it requires a means for measuring the critical pressure by slowly increasing the suction pressure while observing the droplet under the microscope. Fourth, it requires image analysis to measure the radius of the interior capillary chamber and/or the radius of the droplet segment that lies outside the interior capillary chamber, and the internal capillary radius. Fifth, the droplet capture and image analysis operations require manual intervention with well-trained personnel. Sixth, the droplet capture and image analysis operations are not suited for high temperature and pressure conditions.

Another method of measuring interfacial tension using a micropipette has been described in Lee, S., Kim, D. H., and Needham, D., "Equilibrium and Dynamic Interfacial Tension Measurements at Microscopic Interfaces Using a Micropipet Technique. 1. A New Method for Determination of Interfacial Tension," Langmuir 2001, 17(18), pp. 5537-5543. In this method, the meniscus of the interface of a two-phase system is optically observed in a taped micropipette, and the radius of curvature of the meniscus of the interface is measured together with the pressure necessary to maintain the interface at the same position. From the pressure and the curvature, the interfacial tension ($\gamma$) can be calculated by the Laplace equation as follows:

$$\gamma = \frac{R1 \Delta P1}{2} \quad (2)$$

where R1 is the radius of curvature of the meniscus of the interface geometry, and $\Delta$P1 is the pressure necessary to maintain the interface in equilibrium.

The radius of curvature of the meniscus can measured at different pressures. The slope of the pressure versus radius of curvature curve can be used to determine the interfacial tension ($\gamma$) with higher precision because of the multiple data points. The above-described methodology has some disadvantages. First, it requires human intervention for capturing the interface and maintaining it in a stationary position within the micropipette. Second, it requires a means for measuring the pressure $\Delta$P1 with the interface maintained in the stationary position within the micropipette. Third, it requires image analysis to measure the radius of curvature of the meniscus while the interface is maintained in the stationary position within the micropipette. Fourth, the measurement and image analysis operations require manual intervention with well-trained personnel. Fifth, the measurement and image analysis operations are not suited for high temperature and high pressure conditions.

SUMMARY

An apparatus (and method) is provided for characterizing interfacial tension between a non-wetting phase fluid and a wetting phase fluid of a slug flow, which employs a capillary structure that is configured to contain a slug of the non-wetting phase fluid. The slug has a leading edge meniscus and a trailing edge meniscus, and the capillary structure has a venturi-like section. A pressure sensor is configured to measure differential pressure between first and second locations of the capillary structure. The first location is disposed upstream of the leading edge meniscus of the slug with the leading edge meniscus of the slug contained within the venturi-like section of the capillary structure. The second location is disposed downstream of the trailing edge meniscus of the slug. Data processing means is configured to derive a measure of interfacial tension between the non-wetting phase fluid and the wetting phase fluid of the slug flow based upon the differential pressure measured by the pressure sensor. The measure of interfacial tension between the non-wetting phase fluid and the wetting phase fluid of the slug flow can be based further on the geometry (e.g., diameters) of the capillary structure or calibration of the apparatus.

Advantageously, the data processing means can derive the measure of interfacial tension without measuring the change in radius of the menisci of the slug.

In one embodiment, the pressure sensor can be adapted to measure a static differential pressure between the first and second locations of the capillary structure, and the data processing means can be configured to derive the measure of the static interfacial tension between the non-wetting phase fluid and the wetting phase fluid based on the static differential pressure measured by the pressure sensor. To establish the equilibrium needed for obtaining the static interfacial tension, the flow rate of the slugs should approach zero or the flow of the slugs should be stopped for a period before and during the pressure readings.

In another embodiment, the pressure sensor can be adapted to measure a plurality of dynamic differential pressures between the first and second locations of the capillary structure at different flow rates of the slug flow; and the data processing means can be adapted to derive a plurality of dynamic interfacial tensions between the non-wetting phase fluid and the wetting phase fluid of the slug flow as a function of the flow rate based upon the plurality of differential pressures measured by the pressure sensor. In a later stage of the assessment of the results, the lifetime of the interfaces can be deduced from the flow rates, the geometry of the configuration, and phase properties, and finally the dynamic interfacial tension can be obtained as a function of the lifetime of the interface. The prerequisite of this assessment is the establishment of a detailed hydrodynamic model, which describes the rates of interface expansion and compression on the leading and trailing edges of the menisci respectively.

The capillary structure can be configured to allow for flow of the slug flow through the capillary structure.

In a first embodiment, the capillary structure comprises three co-axial cylindrical sections including an intermediate cylindrical section disposed between two outer cylindrical sections. The two outer cylindrical sections have a larger diameter than the intermediate cylindrical section. The intermediate cylindrical section is the venturi-like section. The capillary structure can be oriented such that the three co-axial cylindrical sections extend in a horizontal direction. Alternatively, the capillary structure can be oriented such that the three co-axial cylindrical sections extend in a vertical direction. Alternatively, a non-coaxial arrangement of the cylinders can also be considered.

In this first embodiment, the measure of interfacial tension between the non-wetting phase fluid and the wetting phase fluid of the slug flow can be calculated by the data processing means according to the following equation:

$$\Delta P = 2\gamma \left( \frac{1}{R_{P1}} - \frac{1}{R_{P2}} \right),$$

where $\gamma$ is the measure of interfacial tension between the non-wetting phase fluid and the wetting phase fluid of the slug flow,
$\Delta P$ is a static differential pressure between the first and second locations of the capillary structure,
$R_{P1}$ is the radius of the intermediate cylindrical section of the capillary structure, and
$R_{P2}$ is the radius of the outer cylindrical sections of the capillary structure.

In this first embodiment, the measure of interfacial tension between the non-wetting phase fluid and the wetting phase fluid of the slug flow can also be calculated by the data processing means according to the following equation:

$$\Delta P = \frac{2\gamma}{R_{P1}},$$

where $\gamma$ is the measure of interfacial tension between the non-wetting phase fluid and the wetting phase fluid of the slug flow,
$\Delta P$ is a static differential pressure between the first and second locations of the capillary structure, and
$R_{P1}$ is the radius of the intermediate cylindrical section of the capillary structure.

In the first embodiment, for the case where the capillary structure is oriented such that the three co-axial cylindrical sections extend in a vertical direction, the measure of interfacial tension between the non-wetting phase fluid and the wetting phase fluid of the slug flow can be calculated by the data processing means according to the following equation:

$$\Delta P = \frac{2\gamma}{R_{P1}} - g \left[ L_2 \rho_{wetting} + (L_1 - L_2) \rho_{non\text{-}wetting} + (L_3 - L_1) \rho_{wetting} \right],$$

where $\gamma$ is the measure of interfacial tension between the non-wetting phase fluid and the wetting phase fluid of the slug flow,
$\Delta P$ is a static differential pressure between the first and second locations of the capillary structure,
$R_{P1}$ is the radius of the intermediate cylindrical section of the capillary structure,
$L_1$ is a distance between the first location and the leading edge meniscus of the slug during the measurement of the static differential pressure $\Delta P$,
$L_2$ is a distance between the first location and the trailing edge meniscus of the slug during the measurement of the static differential pressure $\Delta P$,
$L_3$ is the distance between the first location and the second location,
$\rho_{wetting}$ is the density of the wetting phase fluid of the slug flow, and
$\rho_{non\text{-}wetting}$ is the density of the non-wetting phase fluid of the slug flow.

This equation compensates for the effect of gravity on the measurement.

In another embodiment, the venturi-like section of the capillary structure can have a tapered conical form. In this embodiment, the measure of interfacial tension between the non-wetting phase fluid and the wetting phase fluid of the slug flow can be calculated by the data processing means according to the following equation:

$$\Delta p_{12} = 2\gamma \left( \frac{1}{R_1} - \frac{1}{R_2} \right),$$

where $\gamma$ is the measure of interfacial tension between the non-wetting phase fluid and the wetting phase fluid of the slug flow, $\Delta p_{12}$ is a differential pressure between the first and second locations of the conical form venturi-like section of the capillary structure, $R_1$ is the radius of the leading edge meniscus of the slug contained in the venturi-like section of the capillary structure during the measurement of the differential pressure $\Delta p_{12}$, $R_2$ is the radius of the trailing edge meniscus of the slug contained in the venturi-like section of the capillary structure during the measurement of the differential pressure $\Delta p_{12}$, $R_1$ and $R_2$ are related by a mathematical model of droplet motion in the capillary structure, and the differential pressure $\Delta p_{12}$ is related to the measure of interfacial tension $\gamma$ by a parametric function determined from experimental results.

DETAILED DESCRIPTION

Figure 1:
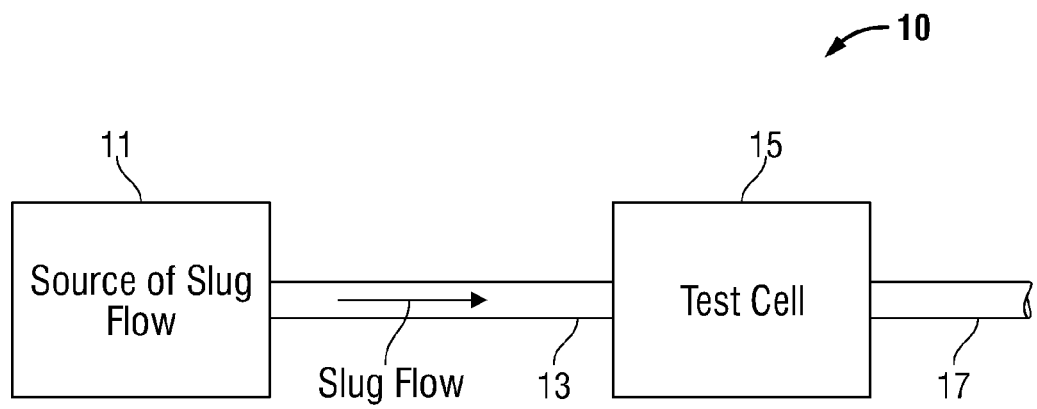
FIG. 1 is a schematic block diagram of a fluid analysis apparatus according to the present application.

FIG. 1 is a schematic view of a fluid analysis system in accordance with the present application. The system 10 includes a source of slug flow 11, a connector tube 13, a flow-through test cell 15, and an exhaust tube 17. The source 11 generates a slug flow of two immiscible or partially miscible fluids where one fluid is a wetting phase that wets the fluid-contacting surfaces of at least the capillary structure of the test cell 15 and the other fluid is a non-wetting phase that does not wet the fluid-contacting surfaces of at least the capillary structure of the test cell 15. The slug flow is characterized by a series of slugs of the non-wetting phase fluid separated by pockets of the wetting phase fluid. The slug flow can be an oil-water emulsion with oil slugs separated by pockets of an aqueous phase. Alternatively, the slug flow can be a water-oil emulsion with aqueous slugs separated by pockets of an oil phase. A surfactant can be part of the slug flow. The source 11 can be realized by microfluidic pumps together with a microfluidic device. The microfluidic pumps feed the flow of the wetting phase fluid, the non-wetting phase fluid, and possibly one or more surfactants to the microfluidic device. The microfluidic device produces the slug flow as monodispersed droplets (slugs) of the non-wetting phase fluid in the wetting phase fluid. The surfactant can be dissolved either in the wetting or in the non-wetting phase. Alternatively the surfactant can be dissolved in both the wetting and non-wetting phases. Yet another alternative is that the surfactant is dissolved in one or both of the phases, then an equilibration time is allowed for the two-phase system to reach a state of equilibrium between the bulk of the phases and the interfaces. During this equilibration process, the surfactant may migrate from the bulk of the phases to the interface, or from the interface to the bulk of the phases, or from one phase to another phase. Alternatively, the migration may involve the combination of all the above-mentioned migration steps. The size (diameter) of the droplets (slugs) that are produced by the microfluidic device can be automatically controlled, for example in a range of 10 to 250 μm. Such systems are sold commercially by The Dolomite Centre Limited of Royston, UK. Alternatively, a suitable stirred chamber can be used to generate the slug flow. In this chamber, an emulsion is formed because of the stirring. The stirring is a generally applied procedure in the industry for emulsion generation from two non-mixable or partially mixable phases. The formation of emulsions is easier when the interfacial tension between the phases is lower. The presence of surfactants leads to reduced interfacial tension and supports the generation of emulsions in the stirred chamber. For applications where the slugs are formed by an aqueous non-wetting phase, the surfaces of the source 11 that define the flow path of the slug flow can be hydrophobic in nature (i.e., strongly oil-wetting). For applications where the slugs are formed by an oil non-wetting phase, the surfaces of the source 11 that define the flow path of the two-phase slug flow can be hydrophilic in nature (i.e., strongly water-wetting).

The connector tube 13 supplies the slug flow produced by the source 11 to the test cell 15. The connector tube 13 is preferably of sufficient length to allow the fluids of the slug flow to equilibrate before entering the test cell 15. For applications where the slugs are formed by an aqueous non-wetting phase, the surfaces of the connector tube 13 that define the flow path of the slug flow can be hydrophobic in nature (i.e., strongly oil-wetting). For applications where the slugs are formed by an oil non-wetting phase, the surfaces of the connector tube 13 that define the flow path of the slug flow can be hydrophilic in nature (i.e., strongly water-wetting).

The test cell 15 defines a flow path that receives the slug flow supplied by the connector tube 13. For applications where the slugs are formed by an aqueous non-wetting phase, the surfaces of the test cell 15 that define the flow path of the slug flow can be hydrophobic in nature (i.e., strongly oil-wetting). For applications where the slugs are formed by an oil non-wetting phase, the surfaces of the test cell 15 that define the flow path of the slug flow can be hydrophilic in nature (i.e., strongly water wetting). The flow path of the test cell 15 includes a capillary structure with a venturi-like (narrowing smaller diameter) section disposed downstream of a wider (larger diameter) section. The capillary structure is arranged to contain a slug of the non-wetting phase of the slug flow in a configuration where the leading edge meniscus of the slug lies in the venturi-like section of the capillary structure and the trailing edge meniscus of the slug lies in the wider section of the capillary structure. The test cell 15 also includes a pressure sensor that measures the pressure differential of the wetting phase of the slug flow adjacent or near the leading and trailing edge menisci of the slug. As long as the measurement locations of the pressure sensor are within the wetting phase and the static differential pressure is measured under no flow conditions, there is no restriction on the position of the measurement locations of the pressure sensor relative to the position of the menisci. When the differential pressure measurement is performed under dynamic conditions, i.e. when there is a continuous flow in the system, the continuous flow causes an axial hydrostatic pressure drop in the capillary structure which is proportional to the distance between the meniscus and the respective measurement location of the pressure sensor. This distance can be configured such that the axial hydrostatic pressure drop in the capillary structure is negligible as compared to the differential pressure measured by the pressure sensor. The test cell 15 further includes processor means (such as a microprocessor, microcontroller or other suitable data processing apparatus) that is adapted to derive a measure of the interfacial tension between the non-wetting phase fluid and the wetting phase fluid of the slug flow based upon the pressure difference measured by the pressure sensor and the geometry of the capillary structure. The measurement of interfacial tension can be repeated for multiple slugs in the slug flow. For example, the measurement of interfacial tension can be repeated for a number of slugs and the resultant measurements averaged to characterize the interfacial tension between the non-wetting phase fluid and the wetting phase fluid of the slug flow. The flow path of the test cell 15 can exit to an exhaust tube 17 that provides for outflow of the slug flow as needed. For example, the exhaust tube 17 can empty into a container that contains the slug flow that flows through the system.

The test cell 15 can be operated in a static mode where the slug flow is controlled (i.e., stopped) such that a slug is maintained in the capillary structure of the test cell 15 with the leading edge meniscus of the slug positioned in the narrower section of the capillary structure and the trailing edge meniscus of the slug positioned in the wider section of the capillary structure. With the slug in this position, the pressure sensor measures the static pressure differential of the wetting phase fluid adjacent the leading and trailing edge menisci of the slug. The processor means of the test cell 15 is adapted to derive a measure of the interfacial tension between the non-wetting phase fluid and the wetting phase fluid of the slug flow based upon the static pressure difference measured by the pressure sensor and the geometry of the capillary structure. This measurement can be repeated in a sequential manner for the next slug (or one or more subsequent slugs) in the slug flow. The flow can be controlled by valves placed either in the connector tube 13 or in the exhaust tube 17 or both the connector tube or exhaust tube. At closed positions of either of these valves, a static pressure differential can be measured.

Figure 2:
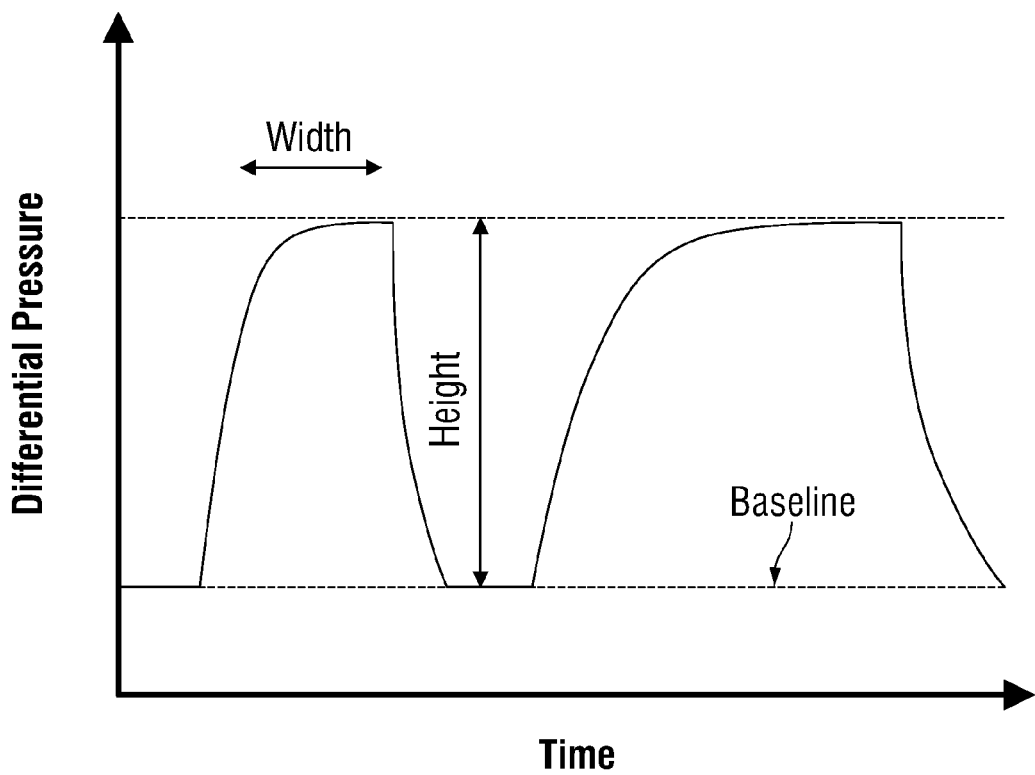
FIG. 2 is a diagram of dynamic differential pressures measured by a pressure sensor of the test cell of FIG. 1.

Alternatively, the test cell 15 can be operated in a continuous mode where the slug flow flows continuously through the capillary structure of the test cell 15 and the differential pressure measurements are made by the pressure sensor over time during such continuous slug flow. In this continuous operational mode, as a given slug passes through the capillary structure, the given slug is contained in the capillary structure with the leading edge meniscus of the slug positioned in the narrower section of the capillary structure and the trailing edge meniscus of the slug positioned in the wider section of the capillary structure. The containment of the given slug in this position within the capillary structure causes a pressure increase transient signal in the differential pressure measured by the pressure sensor relative to a baseline differential pressure as shown in FIG. 2. The baseline differential pressure represents the differential pressure when the wetting phase fluid alone (without the slug of the non-wetting phase fluid) is contained within the capillary structure between the pressure measurement points of the pressure sensor. The pressure increase transient signal is caused when the slug is contained within the capillary structure between the pressure measurement points of the pressure sensor. During this process, the differential pressure increases as the curvature of the leading edge meniscus of the slug is changing. When the radius of curvature of the leading edge meniscus of the slug becomes equal to the internal radius of the narrow capillary section (this is the case for a fluid pair for which the contact angle becomes either zero or 180° depending on the convention of the contact angle definition) and the trailing edge meniscus is positioned in the wider section of the capillary structure, the differential pressure reaches a plateau. At a given capillary geometry and configuration, the width of this plateau is proportional to the volume of the slug, while the height of the plateau is proportional to the interfacial tension between the non-wetting phase fluid and the wetting phase fluid of the slug flow. The processor means of the test cell 15 can be adapted to derive a measure of the interfacial tension between the non-wetting phase fluid and the wetting phase fluid of the slug flow based upon the geometry of the capillary structure and the magnitude (e.g., height) of the pressure increase transient signal relative to the baseline pressure difference signal as measured by the pressure sensor. Because this measurement of interfacial tension is performed under flow conditions, it is a measure of dynamic interfacial tension, which is usually higher than the static (i.e., equilibrium) interfacial tension measured by the static mode as described above. In this case, the processor means of the test cell 15 can be configured to measure the magnitude (e.g., height) of the pressure increase transient signal relative to the baseline pressure difference signal at a number of different flow rates. Such pressure differences can be plotted as a function of flow rate and extrapolated to zero flow rate to provide a pressure difference for zero flow rate. A measure of the static interfacial tension between the non-wetting phase fluid and the wetting phase fluid of the slug flow can be based upon the geometry of the capillary structure and the zero flow rate pressure difference provided by extrapolation.

Figure 3:
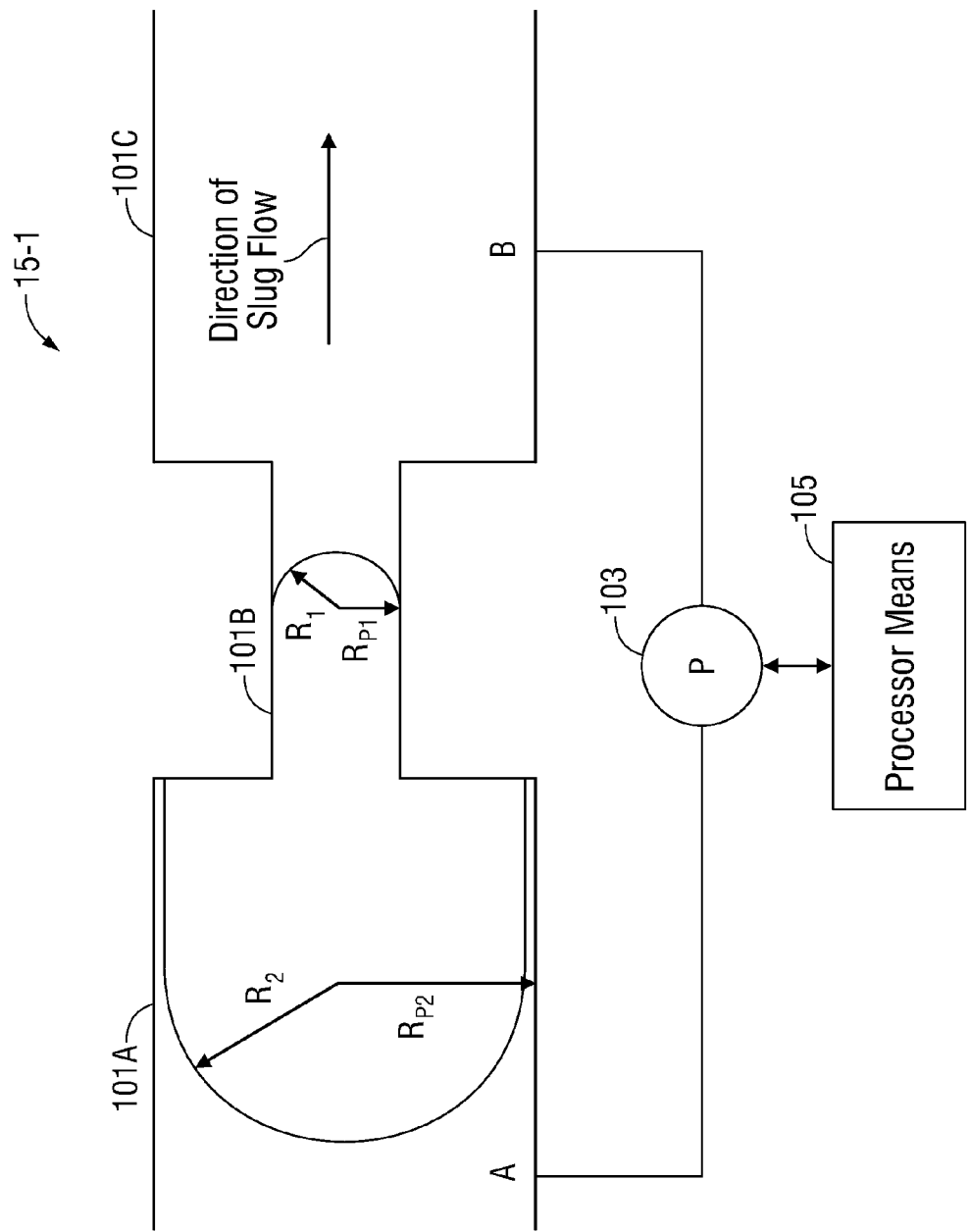
FIG. 3 is a schematic diagram of a first embodiment of the test cell of FIG. 1.

A first embodiment of the capillary structure of a test cell 15-1 is shown in FIG. 3. It includes three cylindrical capillary sections 101A, 101B, and 101C. For the sake of simplicity, these cylindrical capillary sections are represented in FIG. 3 as co-axial. Nevertheless, non-coaxial configurations are also feasible. The three coaxial cylindrical capillary sections 101A, 101B, and 101C are preferably mounted or otherwise secured in a horizontal orientation (perpendicular to a vertical orientation and the effect of gravity). Outer capillary sections 101A and 101C have a large radius labeled $R_{P2}$ as shown. Intermediate section 101B extends between the two outer sections 101A and 101C and has a smaller radius labeled $R_{P1}$ (whereby $R_{P2} > R_{P1}$) to form a venturi-tube-like configuration as shown. The three coaxial cylindrical capillary sections 101A, 101B, and 101C are arranged to contain a slug of the non-wetting phase fluid of the slug flow in a configuration where the leading edge meniscus of the slug lies in the venturi-like section 101B and the trailing edge meniscus of the slug lies in the wider section 101A as shown. The test cell 15-1 also includes a pressure sensor 103 that measures the pressure differential of the wetting phase fluid between locations A and B. Location A is located in the wider section 101A and disposed adjacent or near the trailing edge meniscus of the slug. Location B is located in the wider section 101C and disposed upstream of the leading edge meniscus of the slug. Alternatively, location B can be in the narrower capillary section as long as point B is still within the wetting phase. However, identifying the position of the meniscus in the narrower section can be challenging because of the need for visual observation. As long as the measurement locations A, B of the pressure sensor 103 are within the wetting phase and the static differential pressure is measured under no flow conditions, there is no restriction on the measurement locations of the pressure sensor 103 relative to the position of the menisci. When the differential pressure measurement is performed under dynamic conditions, i.e. when there is a continuous flow in the system, the continuous flow causes an axial hydrostatic pressure drop in the capillary sections which is proportional to the distance between the meniscus and the respective measurement location of the pressure sensor 103. This distance can be configured such that the axial hydrostatic pressure drop in the capillary sections is negligible as compared to the differential pressure measured by the pressure sensor 103. Test cell 15-1 also includes processor means 105 (such as a microprocessor, microcontroller, or other suitable data processing apparatus) that is adapted to derive a measure of the interfacial tension between the non-wetting phase fluid and the wetting phase fluid of the slug flow based upon the geometry of the capillary sections 101A, 101B, and 101C and the pressure difference measured by the pressure sensor 103. The measurement of interfacial tension can be repeated for one or more slugs in the slug flow.

Test cell 15-1 can be operated in a static mode where the slug flow is controlled (i.e., stopped) such that a slug is maintained in the capillary sections of the test cell 15-1 in a configuration where the leading edge meniscus of the slug lies in the narrow intermediate section 101B and the trailing edge meniscus of the slug lies in the wider section 101A as shown in FIG. 3. With the slug in this position, the pressure sensor 103 measures the static pressure differential of the wetting phase fluid between locations A and B as described above. The processor means 105 of the test cell 15-1 is adapted to derive a measure of the interfacial tension between the non-wetting phase fluid and the wetting phase fluid of the slug flow based upon the geometry of the cylindrical capillary sections 101A, 101B, and 101C and the static pressure difference measured by the pressure sensor 103. This measurement can be repeated in a sequential manner for the next slug (or one or more subsequent slugs) in the slug flow.

The processor means 105 can relate the static pressure difference ($\Delta P$) measured by the pressure sensor 103 to the interfacial tension ($\gamma$) between the non-wetting phase fluid and the wetting phase fluid of the slug flow based on the Laplace equation:

$$\Delta P = 2\gamma\left(\frac{1}{R1} - \frac{1}{R2}\right) \quad (3)$$

where R1 is the radius of curvature of the leading edge meniscus of the slug, and R2 is the radius of curvature of the trailing edge meniscus of the slug.

Equation (3) is the limited form of a more complex Laplace equation, because here it is assumed that the leading edge and trailing edge menisci have cylindrical symmetry because the capillary sections 101A and 101B have cylindrical symmetry. Equation (3) further assumes that the effect of gravity has no impact on the curvature of the leading edge and trailing edge menisci. This condition can be satisfied when the Eotvos number (Eo) is smaller than 1. The Eotvos number is defined by the following expression:

$$Eo = (\Delta\rho g L^2)/\gamma \quad (4)$$

where $\Delta\rho$ is the difference in density of the non-wetting phase fluid and wetting phase fluid of the slug flow, g is gravitational acceleration, and L is the diameter of the capillary.

In practice, this condition can be satisfied when the interfacial tension $\gamma$ is sufficiently high and/or the capillary diameter is sufficiently small.

Equation (3) also assumes that the wetting phase fluid of the slug flow perfectly wets the interior surface of the capillary structure; hence, the contact angle of the wetting phase is zero on the interior surface. This condition can be ensured with proper material selection, and/or chemical treatment, and/or suitable mechanical patterns for the interior surface of the capillary sections 101A, 101B, 101C. For example, details of such structures for oil-wetting surfaces are described in Ke, Q., Fu, W., Jin, H., Zhang, L., Tang, T., Zhang, J., "Fabrication of mechanically robust superhydrophobic surfaces based on silica micro-nanoparticles and polydimethylsiloxane," *Surface and Coatings Technology* 205 (21-22), pp. 4910-4914 (2011).

In the event that these conditions are satisfied (i.e., that the leading edge and trailing edge menisci have cylindrical symmetry, that the effect of gravity has no impact on the curvature of the leading edge and trailing edge menisci, and the wetting phase fluid of the slug flow perfectly wets the interior surface of the capillary structure), Equation (3) can be simplified by assuming that the radius of curvature of the leading edge meniscus of the slug (R1) is equal to the radius $R_{P1}$ of the narrow section 101B of the test cell 15-1 and that the radius of curvature of the trailing edge meniscus of the slug (R2) is equal to the radius $R_{P2}$ of the wider section 101A of the test cell 15-1, which gives:

$$\Delta P = 2\gamma\left(\frac{1}{R_{P1}} - \frac{1}{R_{P2}}\right) \quad (5)$$

where $R_{P1}$ is the radius of the narrow section 101B, and $R_{P2}$ is the radius of the wider section 101A.

For this case, the processor means 105 can calculate the interfacial tension ($\gamma$) from the static pressure difference ($\Delta P$) measured by the pressure sensor and the known capillary radii $R_{P1}$ and $R_{P2}$.

Alternatively, test cell 15-1 can be operated in a continuous mode where the slug flow continuously flows through the capillary sections 101A, 101B, and 101C of the cell 15-1 and the differential pressure measurements are made by the pressure sensor 103 over time during such continuous slug flow. In this continuous operational mode, as a given slug passes through the capillary structure, the given slug is contained in the capillary structure with the leading edge meniscus of the slug positioned in the venturi-like section 101B and the trailing edge meniscus of the slug positioned in the wider section 101A. The containment of the given slug in this position within the capillary structure causes a pressure increase transient signal in the differential pressure measured by the pressure sensor 103 relative to a baseline differential pressure as shown in FIG. 2. The baseline differential pressure represents the differential pressure when the wetting phase fluid alone (without the slug of the non-wetting phase) is contained within the capillary sections 101A, 101B, and 101C between the pressure measurement locations A, B of the pressure sensor 103. The pressure increase transient signal is caused when the slug is contained within the capillary sections 101A, 101B, and 101C between the pressure measurement locations A, B of the pressure sensor 103. The processor means 105 of test cell 15-1 can be adapted to derive a measure of the interfacial tension between the non-wetting phase fluid and the wetting phase fluid of the slug flow based upon the geometry of the capillary sections 101A, 101B, and 101C and the magnitude (e.g., height) of the pressure increase transient signal relative to the baseline pressure difference signal as measured by the pressure sensor 103. For example, Equation (5) can be used where ΔP represents the magnitude (e.g., height) of the pressure increase transient signal relative to the baseline pressure difference signal. Because this measurement of interfacial tension is performed under flow conditions, it is a measure of dynamic interfacial tension, which is usually higher than the static (i.e., equilibrium) interfacial tension measured by the static mode as described above. In this case, the processor means 105 can be configured to measure the magnitude (e.g., height) of the pressure increase transient signal relative to the baseline pressure difference signal at a number of different flow rates. Such pressure differences can be plotted as a function of flow rate and extrapolated to zero flow rate to provide a pressure difference for zero flow rate. A measure of the static interfacial tension between the non-wetting phase fluid and the wetting phase fluid of the slug flow can be based upon the geometry of the capillary sections 101A, 101B, and 101C and the zero flow rate pressure difference provided by extrapolation. For example, the processor means 105 can calculate a measure of static interfacial tension using Equation (5) where ΔP represents the zero flow rate pressure difference provided by such extrapolation.

Figure 4:
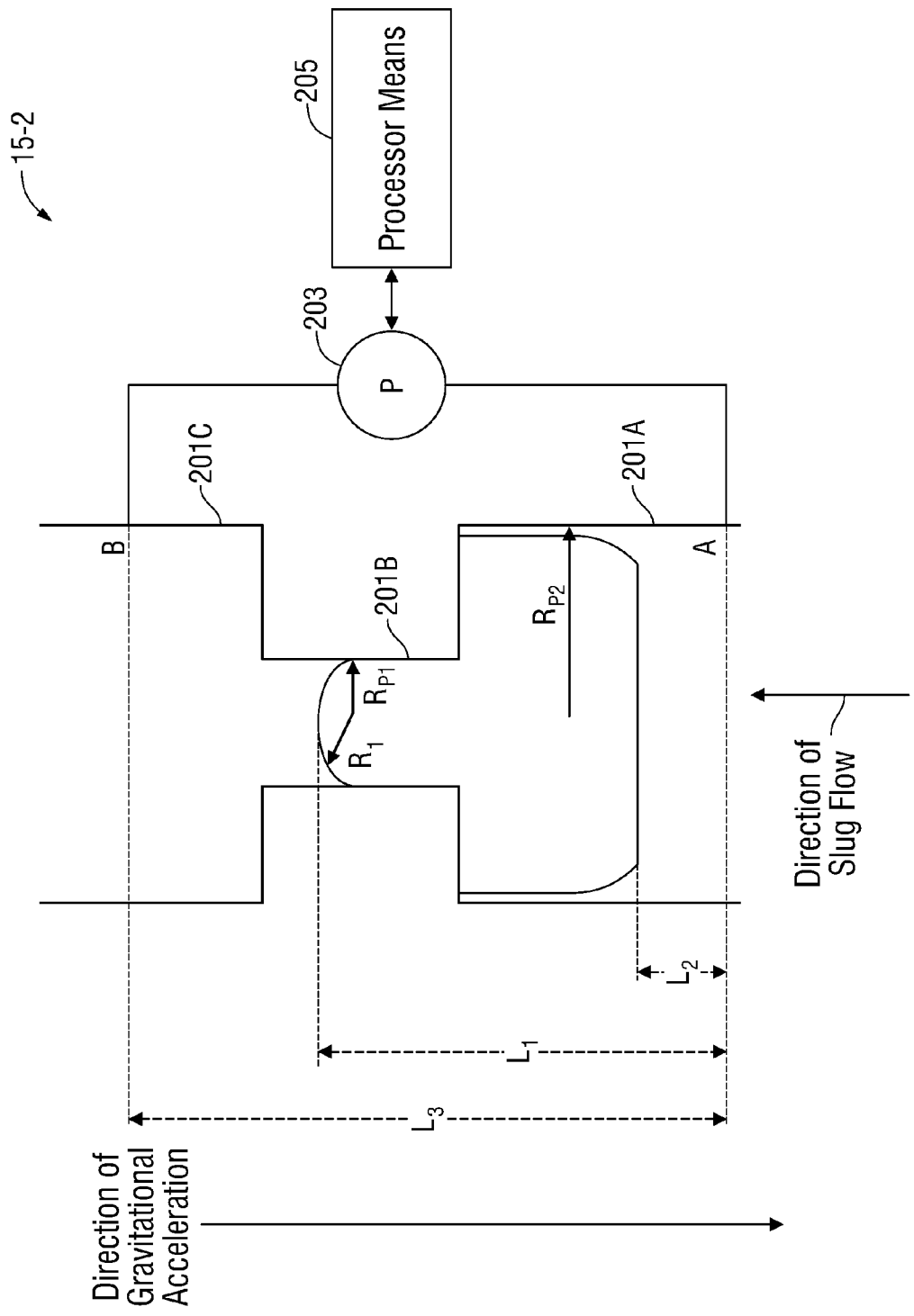
FIG. 4 is a schematic diagram of a second embodiment of the test cell of FIG. 1.

A second embodiment of the capillary structure of a test cell 15-2 is shown in FIG. 4. It includes three coaxial cylindrical capillary sections 201A, 201B, and 201C. For the sake of simplicity, these cylinders are represented in FIG. 4 as coaxial. Nevertheless, non-coaxial configurations are also feasible. The three coaxial cylindrical capillary sections 201A, 201B, and 201C are preferably mounted or otherwise secured in a vertical orientation (aligned with the effect of gravity). Bottom section 201A and top section 201C have a large radius labeled $R_{P2}$ as shown. Intermediate section 201B extends between the bottom section 201A and the top section 201C and has a smaller radius labeled $R_{P1}$ (whereby $R_{P2} > R_{P1}$) to form a venturi-tube-like configuration as shown. The three coaxial cylindrical capillary sections 201A, 201B, and 201C are arranged such that slug flow is upward (against the effect of gravity) and a slug of the non-wetting phase fluid is contained in a configuration where the leading edge meniscus of the slug lies in the venturi-like section 201B and the trailing edge meniscus of the slug lies in the wider section 201A as shown. The test cell 15-2 also includes a pressure sensor 203 that measures the pressure differential of the wetting phase fluid between locations A and B. Location A is located in the bottom section 201A and disposed adjacent or near the trailing edge meniscus of the slug. Location B is located in the top section 201C and disposed upstream of the leading edge meniscus of the slug. Alternatively, location B can be in the narrower capillary section as long as point B is still within the wetting phase. However, identifying the position of the meniscus in the narrower section can be challenging because of the need for visual observation. As long as the measurement locations A, B of the pressure sensor 203 are within the wetting phase and the static differential pressure is measured under no flow conditions, there is no restriction on the measurement locations of the pressure sensor 203 relative to the position of the menisci. When the differential pressure measurement is performed under dynamic conditions, i.e. when there is a continuous flow in the system, the continuous flow causes an axial hydrostatic pressure drop in the capillary sections which is proportional to the distance between the meniscus and the respective measurement location of the pressure sensor 203. This distance can be configured such that the axial hydrostatic pressure drop in the capillary sections is negligible as compared to the differential pressure measured by the pressure sensor 203. The test cell 15-2 also includes a processor means 205 that is adapted to derive a measure of the interfacial tension between the non-wetting phase fluid and the wetting phase fluid of the slug flow based upon the geometry of the capillary sections 201A, 201B, and 201C and the pressure difference measured by the pressure sensor 203. The measurement of interfacial tension can be repeated for one or more slugs in the slug flow.

The test cell 15-2 can be operated in a static mode where the slug flow is controlled (i.e., stopped) such that a slug is maintained in the capillary sections of the test cell 15-2 in a configuration where the leading edge meniscus of the slug lies in the narrow intermediate section 201B and the trailing edge meniscus of the slug lies in the wider bottom section 201A as shown in FIG. 4. With the slug in this position, the pressure sensor 203 measures the static pressure differential of the wetting phase fluid between locations A and B as described above. The processor means 205 of the test cell 15-2 can be adapted to derive a measure of the interfacial tension between the non-wetting phase fluid and the wetting phase fluid of the slug flow based upon the geometry of the cylindrical capillary sections 201A, 201B, and 201C and the static pressure difference measured by the pressure sensor 203. This measurement can be repeated in a sequential manner for the next slug (or one or more subsequent slugs) in the slug flow.

The processor means 205 can relate the static pressure difference (ΔP) measured by the pressure sensor 203 to the interfacial tension (γ) between the non-wetting phase fluid and the wetting phase fluid of the slug flow based on the Laplace Equation (3) as described above. Equation (3) is the limited form of a more complex Laplace equation, because here it is assumed that the leading edge and trailing edge menisci have cylindrical symmetry because the capillary sections 201A and 201B have cylindrical symmetry. Equation (3) further assumes that the effect of gravity has no impact on the curvature of the leading edge meniscus. This condition can be satisfied when the Eotvos number is smaller than 1 for the narrower capillary section. In practice, this condition can be satisfied when the interfacial tension γ is sufficiently high and/or the capillary radiuses are sufficiently small. Equation (3) also assumes that the wetting phase fluid perfectly wets the interior surface of the capillary structure; hence, the contact angle of the wetting phase is zero on the interior surface. This condition can be ensured with either proper material selection, or chemical treatment, or suitable mechanical patterns for the interior surface of the capillary sections 201A, 201B, 201C as described above.

Moreover, in the vertical arrangement of FIG. 4, the trailing edge meniscus becomes flat in the wider section 201A of the test cell 15-2, which means that the radius of curvature of trailing edge meniscus of the slug approaches infinity. This is the case when the Eotvos number is significantly higher for the wider capillary section. This assumption allows Equation (3) to be simplified as:

$$\Delta P = \frac{2\gamma}{R1}, \tag{6}$$

where R1 is the radius of curvature of the leading edge meniscus of the slug.

In the event that these conditions are satisfied (i.e., that the leading edge and trailing edge menisci have cylindrical symmetry, that the effect of gravity has no impact on the curvature of the leading edge meniscus, the curvature of the radius of the trailing edge meniscus approaches infinite at the point of the axis of the wider cylindrical capillary, and the wetting phase fluid of the slug flow perfectly wets the interior surface of the capillary structure), Equation (6) can be simplified by assuming that the radius of curvature of the leading edge meniscus of the slug is equal to the radius $R_{P1}$ of the narrow section 201B of the test cell 15-2 as:

$$\Delta P = \frac{2\gamma}{R_{P1}} \quad (7)$$

where $R_{P1}$ is the radius of the narrow section 201B of the test cell 15-2.

For this case, the processor means 205 can calculate interfacial tension ($\gamma$) from the static pressure difference ($\Delta P$) measured by the pressure sensor 203 and the known capillary radius $R_{P1}$.

For the vertical configuration of FIG. 4, the effect of gravity on the calculation of the interfacial tension ($\gamma$) can be corrected with the following formula:

$$\Delta P = \frac{2\gamma}{R_{P1}} - g\left[L_2 \rho_{wetting} + (L_1 - L_2)\rho_{non\text{-}wetting} + (L_3 - L_1)\rho_{wetting}\right] \quad (8)$$

where $R_{P1}$ is the radius of the narrow section 201B of the test cell 15-2;

$L_1$, $L_2$, and $L_3$ are distances as shown in FIG. 4;

$\rho_{wetting}$ is the density of the wetting phase fluid of the slug flow; and $\rho_{non\text{-}wetting}$ is the density of the non-wetting phase fluid of the slug flow.

The distances $L_1$ and $L_2$ can be measured by optical means by magnifying the image of the cell 15-2. Although an optical technique can be used here to obtain the said distances, it is important to realize that the demand for the resolution of the optical means is less than the resolution required to obtain the curvature of the interface optically as described in the prior art. Hence, the recommended approach is less demanding, therefore, more advantageous than the methodology described in the prior art. The distance $L_3$ is known by design. The densities of the wetting and non-wetting phase fluids can be measured or known from tables. For this case, the processor means 205 can calculate interfacial tension ($\gamma$) using Equation (8) with the static pressure difference ($\Delta P$) measured by the pressure sensor 203, the measured distances $L_1$ and $L_2$, the densities of the wetting and non-wetting phase fluids, the known distance $L_3$, and the capillary radius $R_{P1}$.

Alternatively, the test cell 15-2 can be operated in a continuous mode where the slug flow flows continuously through the capillary sections 201A, 201B, and 201C of the cell 15-2 and the differential pressure measurements are made by the pressure sensor 203 over time during such continuous slug flow. In this continuous operational mode, as a given slug passes through the capillary structure, the given slug is contained in the capillary structure with the leading edge meniscus of the slug positioned in the venturi-like section 201B and the trailing edge meniscus of the slug positioned in the wider section 201A. The containment of the given slug in this position within the capillary structure causes a pressure increase transient signal in the differential pressure measured by the pressure sensor relative to a baseline differential pressure as shown in FIG. 2. The baseline differential pressure represents the differential pressure when the wetting phase fluid alone (without the slug of the non-wetting phase) is contained within the capillary sections 201A, 201B, and 201C between the pressure measurement locations A, B of the pressure sensor 203. The pressure increase transient signal is caused when the slug is contained within the capillary sections 201A, 201B, and 201C between the pressure measurement locations A, B of the pressure sensor 203. The processor means 205 of the test cell 15-2 can be adapted to derive a measure of the interfacial tension between the non-wetting phase fluid and the wetting phase fluid of the slug flow based upon the geometry of the capillary sections 201A, 201B, and 201C and the magnitude (e.g., height) of the pressure increase transient signal relative to the baseline pressure difference signal as measured by the pressure sensor 203. For example, the processor means 205 can calculate interfacial tension ($\gamma$) from Equation (7) where $\Delta P$ represents the magnitude (e.g., height) of the pressure increase transient signal relative to the baseline pressure difference signal. Because this measurement of interfacial tension is performed under flow conditions, it is a measure of dynamic interfacial tension, which is usually higher than the static (i.e., equilibrium) interfacial tension measured by the static mode as described above. In this case, the processor means 205 can be configured to measure the magnitude (e.g., height) of the pressure increase transient signal relative to the baseline pressure difference signal at a number of different flow rates. Such pressure differences can be plotted as a function of flow rate and extrapolated to zero flow rate to provide a pressure difference for zero flow rate. A measure of the static interfacial tension between the non-wetting phase fluid and the wetting phase fluid of the slug flow can be based upon the geometry of the capillary sections 201A, 201B, and 201C and the zero flow rate pressure difference provided by extrapolation. For example, the processor means 205 can calculate a measure of the static interfacial tension using Equation (7) where $\Delta P$ represents the zero flow rate pressure difference provided by such extrapolation.

Figure 5:
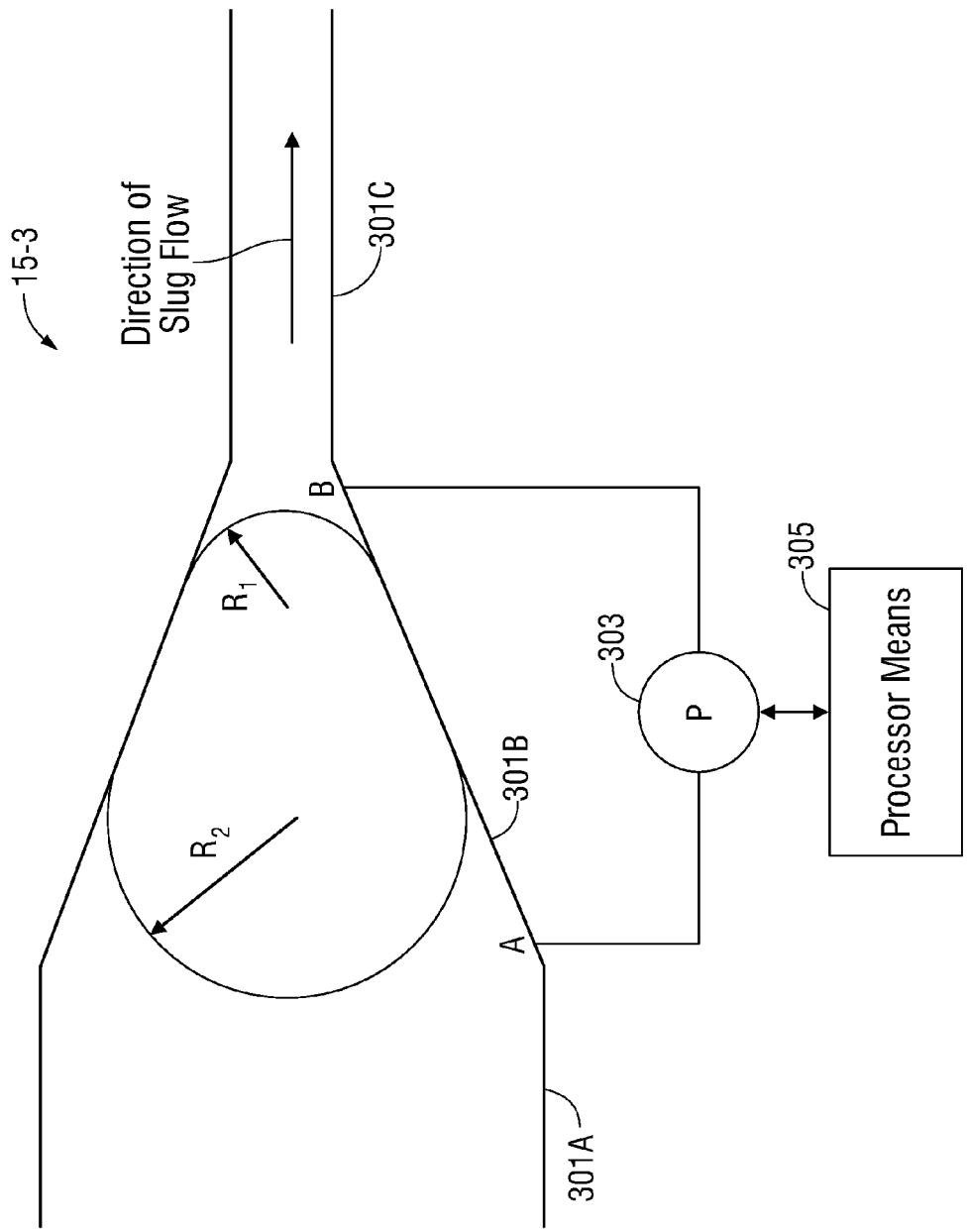
FIG. 5 is a schematic diagram of a third embodiment of the test cell of FIG. 1.

A third embodiment of the capillary structure of a test cell 15-3 is shown in FIG. 5. It includes three coaxial capillary sections 301A, 301B, and 301C. The three coaxial capillary sections 301A, 301B, and 301C can be mounted or otherwise secured in a horizontal orientation (perpendicular to vertical and the effect of gravity), or possibly secured in a vertical orientation (aligned with the effect of gravity). Cylindrical section 301A has large radius and cylindrical section 301C has a small radius smaller than the large radius of section 301A. Intermediate venturi-like section 301B has a tapered conical form that tapers from the large radius of section 301A to the small radius of section 301C as shown. The venturi-like section 301B is arranged to contain a slug of the non-wetting phase fluid in a configuration where both the leading edge and trailing edge menisci of the slug lie in the tapered conical form section 301B as shown. The test cell 15-3 also includes a pressure sensor 303 that measures the pressure differential of the perfectly wetting phase fluid between locations A and B. Location A is located in the section 301B and disposed adjacent or near the trailing edge meniscus of the slug. Location B is located in the section 301B and disposed upstream of the leading edge meniscus of the slug. As long as the measurement locations A, B of the pressure sensor 303 are within the wetting phase and the static differential pressure is measured under no flow conditions, there is no restriction on the measurement locations of the pressure sensor 303 relative to the position of the menisci. When the differential pressure measurement is performed under dynamic conditions, i.e. when there is a continuous flow in the system, the continuous flow causes an axial hydrostatic pressure drop in the capillary sections which is proportional to the distance between the meniscus and the respective measurement location of the pressure sensor 303. This distance can be configured such that the axial hydrostatic pressure drop in the capillary sections is negligible as compared to the differential pressure measured by the pressure sensor 303. The test cell 15-3 also includes processor means 305 (such as a microprocessor, microcontroller, or other suitable data processing apparatus) that is adapted to derive a measure of the interfacial tension between the non-wetting phase fluid and the wetting phase fluid of the slug flow based upon the geometry of the capillary section 301B and the pressure difference measured by the pressure sensor 303. The measurement of interfacial tension can be repeated for one or more slugs in the slug flow.

The test cell 15-3 can be operated in a static mode where the slug flow is controlled (i.e., stopped) such that a slug is maintained in the capillary section 301B of the test cell 15-3 in a configuration where both the leading edge and trailing edge menisci of the slug lie in the conical form section 301B as shown in FIG. 5. With the slug in this position, the pressure sensor 303 measures the static pressure differential of the perfectly wetting phase fluid between locations A and B as described above. The processor means 305 of the test cell 15-3 can be adapted to derive a measure of the interfacial tension between the non-wetting phase fluid and the perfectly wetting phase fluid of the slug flow based upon the geometry of the conical form section 301B and the static pressure difference measured by the pressure sensor 303. This measurement can be repeated in a sequential manner for the next slug (or one or more subsequent slugs) in the slug flow.

Figure 6:
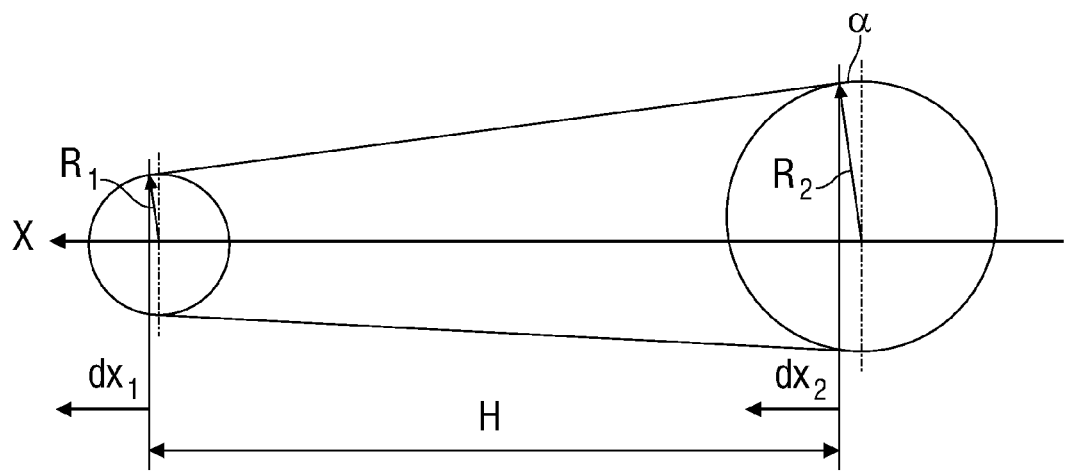
FIG. 6 is a diagram of a model of conical droplet motion resulting from pressure change in a conical form capillary.

A model of conical droplet motion resulting from capillary pressure change can be used as a basis for calculations performed by the processor means 305 that relate such capillary pressure change to interfacial tension (γ) in the capillary structure. In a conical-shaped capillary as depicted schematically in FIG. 6, the equations of droplet motion can be formulated in terms of the evolution of spherically-shaped caps constraining the droplet as:

$$\frac{dR_1}{dx_1} = \sin\alpha \tag{9}$$

$$\frac{dR_2}{dx_2} = \sin\alpha \tag{10}$$

where $$dx_2 = \frac{dR_2}{dx_1}\frac{1}{\sin\alpha}dx_1.$$

A change in the conical part volume due to small displacement of the droplet (the left end of the droplet is displaced on the distance $dx_1$) can be represented by:

$$d(V_{c1} - V_{c2}) = \pi\cos^4\alpha dx_1\left(R_1^2 - R_2^2\frac{dR_2}{dx_1}\frac{1}{\sin\alpha}\right). \tag{11}$$

This change equals the total reduction on the volume of the side caps as:

$$\frac{d(V_1 + V_2)}{dx_1}dx_1 = -\left[\pi R_1^2 \sin\alpha A + \pi R_2^2 \frac{dR_2}{dx_1}(4 - A)\right]dx_1 \tag{12}$$

where $$A = (1 - \sin\alpha)^2(2 + \sin\alpha).$$

Equating the conical part and the caps volume changes yields the following differential equation:

$$R_2^2 \frac{dR_2}{dx_1} = R_1^2 f(\alpha) \tag{13}$$

where $$f(\alpha) = \frac{\sin\alpha\left(\frac{\cos^4\alpha}{\sin\alpha} - A\right)}{4 + \left(\frac{\cos^4\alpha}{\sin\alpha} - A\right)}.$$

The initial conditions for this Equation (12) are:

$$R_1 = R_{10}, \tag{14}$$

$$R_{20} = R_{10} + \frac{H_0}{\cos^2\alpha}\sin\alpha. \tag{15}$$

After taking into account Equation (9), the analytical solution of Equation (13) is easily obtained as:

$$R_2 = \left[R_{20}^3 + \frac{f(\alpha)}{\sin\alpha}(R_1^3 - R_{10}^3)\right]^{\frac{1}{3}} \tag{16}$$

where $$R_1 = R_{10} - x\sin\alpha.$$

The pressure difference between the bubble ends ($\Delta p_{12}$), which represents the differential pressure difference between the interface of the leading edge of the droplet (at $R_1$) and the interface of the trailing edge of the droplet (at $R_2$), can be related to interfacial tension (γ) of the droplet as:

$$\Delta p_{12} = 2\gamma\left(\frac{1}{R_1} - \frac{1}{R_2}\right). \tag{17}$$

For a given taper angle α and given initial condition for $R_{10}$, the pressure difference $\Delta p_{12}$ can be related to the coordinate x for a specific initial condition for $H_0$, and known interfacial tension γ as follows:

$$\Delta p_{12} = g(x,\gamma). \tag{18}$$

Figure 7:
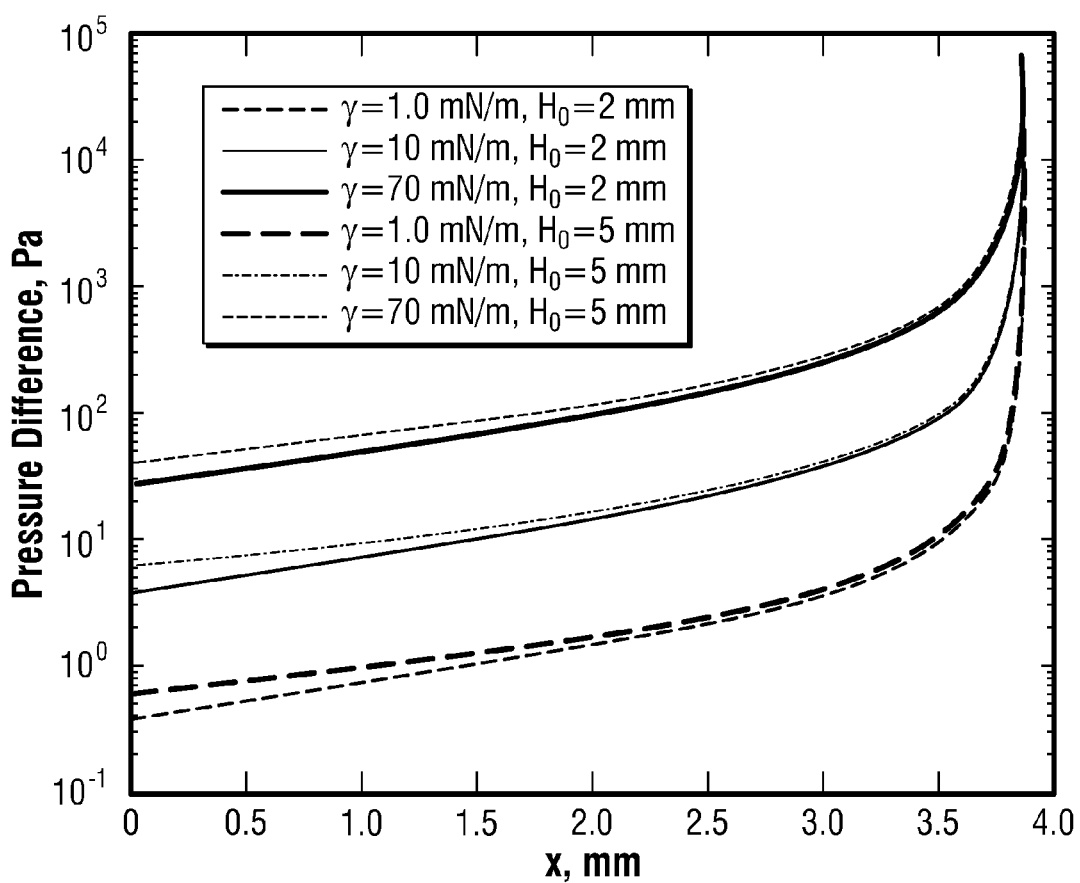
FIG. 7 is a graph of experimental data showing measured differential pressure as a function of axial conical droplet motion for a number of oil-water emulsions with a known interfacial tension and known starting droplet sizes.

The function g(x) of Equation (18) can be derived for different interfacial tensions and different initial conditions for $H_0$ by correlating the results of experiments or simulation that measure the pressure difference $\Delta p_{12}$ as a function of the coordinate x for different interfacial tensions γ and different initial conditions for $H_0$. An example of such simulation results is shown in FIG. 7. In this example, the case of a conical form section 301B having a taper angle α of 15 degrees and droplets having an initial radius $R_{10}$ of 1 mm was investigated by numerical calculation. Because the initial radius has to be significantly larger than the final radius (at least a few hundred times larger) in one part of such simulation, droplets having an initial length $H_0$ of 2 mm with different interfacial tensions ($\gamma$) of 1, 10 and 70 mN/m were calculated. In a second part of such simulation, droplets having an initial length $H_0$ of 5 mm with different interfacial tensions ($\gamma$) of 1, 10 and 70 mN/m were calculated. In both simulation parts, the pressure difference $\Delta p_{12}$ was varied for each drop in order to cause droplet displacement until the smaller radius reaches the value $R_1$ of 1 µm. The curves of FIG. 7 are clearly different from one another for the different surface tensions. At the different droplet initial lengths the curves visibly differ from one another for the low pressure differences only. Hence, the simulation demonstrated the sensitivity of the methodology on the changes in the interfacial tension. In other words, samples with different interfacial tension would yield pressure differences, which are detected by the pressure sensor. In practice, there is no need to vary the initial length. The differential pressures can be read for a number of different droplets of the same system; i.e., having the same interfacial tension. The result data can be correlated to provide the function g(x) of Equation (18) for different surface tensions and different initial condition for $H_0$. The correlations of Equation (18) can be used in conjunction with Equations (15), (16), and (17) to determine the interfacial tension between the non-wetting phase fluid and the wetting phase fluid of the slug flow.

Specifically, the above considerations are used as follows. The initial smallest droplet radius is known, as it corresponds to a certain channel cross-section. After measuring the initial droplet length, the largest droplet radius by Equation (15), the droplet is displaced while simultaneously measuring the pressure difference as a function of the coordinate x. After that the value of the interfacial tension of Equation (18) can be varied to obtain the best match of measured and computed functions. The best match is reached at the most accurate value of the interfacial tension.

Alternatively, the test cell 15-3 can be operated in a continuous mode where the slug flow flows continuously through the capillary sections 301A, 301B, and 301C of the cell 15-3 and the differential pressure measurements are made by the pressure sensor 303 over time during such continuous slug flow. In this continuous operational mode, as a given slug passes through the capillary structure, the given slug is contained in the capillary structure with both the leading edge and trailing edge menisci positioned in the conical form section 301B. The containment of the given slug in this position within the capillary structure causes a pressure increase transient signal in the differential pressure measured by the pressure sensor relative to a baseline differential pressure as shown in FIG. 2. The baseline differential pressure represents the differential pressure when the wetting phase fluid alone (without the slug of the dispersed phase) is contained within the capillary sections 301A, 301B, and 301C between the pressure measurement locations A, B of the pressure sensor 303. The pressure increase transient signal is caused when the slug is contained within the capillary section 301B between the pressure measurement locations A, B of the pressure sensor 303. The processor means 305 of the test cell 15-3 can be adapted to derive a measure of the interfacial tension between the non-wetting phase fluid and the wetting phase fluid of the slug flow based upon the geometry of the capillary section 301B and the magnitude (e.g., height) of the pressure increase transient signal relative to the baseline pressure difference signal as measured by the pressure sensor 303. For example, Equation (18) can be used to provide the best fit of the calculated dependence of the pressure on the droplet displacement to the measured dependence by varying the interfacial tension value in Equation (18). In Equation (18), $\Delta p_{12}$ represents the magnitude (e.g., height) of the pressure increase transient signal relative to the baseline pressure difference signal. Because this measurement of interfacial tension is performed under flow conditions, it is a measure of dynamic interfacial tension, which is usually higher than the static (i.e., equilibrium) interfacial tension measured by the static mode as described above. In this case, the processor means 305 can be configured to measure the magnitude (e.g., height) of the pressure increase transient signal relative to the baseline pressure difference signal at a number of different flow rates. Such pressure differences can be plotted as a function of flow rate and extrapolated to zero flow rate to provide a pressure difference for zero flow rate. A measure of the static interfacial tension between the non-wetting phase fluid and the wetting phase fluid of the slug flow can be based upon the geometry of the capillary section 301B and the zero flow rate pressure difference provided by extrapolation. For example, the processor means 305 can a measure of the static interfacial tension according to Equation (16), where $\Delta p_{12}$ represents the zero flow rate pressure difference provided by such extrapolation.

The pressure sensor of the test cells as described herein can be realized by an electronic differential pressure gauge or other suitable electronic pressure measurement devices. The electronic differential pressure gauge can provide an easily manufacturable alternative and utilizes non-optical sensing technology. It is important to note that many noise and stability issues of the pressure gauge can be avoided by the recommended differential pressure monitoring. Also for high temperature applications, the differential pressure gauge can be placed into a low and controlled temperature environment and it can be connected by long tubing to the high temperature measuring points. This configuration allows heat dissipation and ensures stable sensor response.

In alternate embodiments, the pressure sensor of the test cells can be realized by a u-tube filled with two immiscible liquids of small density difference, a u-tube with capacitance meniscus reading, or other suitable pressure measuring system. The u-tube filled with two immiscible liquids of small density difference can be used under high temperature conditions without technical challenges, but it requires optical reading of the meniscus differences, which is not preferable under high pressure conditions. This optical reading can be performed by a commercially available cathetometer or suitable image analysis software that provides the reading of the meniscus differences using high-resolution photos or video recordings. The u-tube with capacitance meniscus reading employs high and low dielectric permittivity liquids that form the meniscus. The two horizontal sections of the u-tube are inserted within the plates of the capacitors. The capacitors are the parts of a Winston bridge, so the capacity, and hence the meniscus differences, can be read with a non-optical methodology.

The embodiments described above can be used to study the effect of one or more surfactants (and/or different surfactant concentrations) on the interfacial surface tension between the non-wetting phase fluid and the wetting phase fluid of the slug flow. For instance, the surfactant concentration in an aqueous wetting phase fluid of the slug flow can easily be changed by a dual pump injection, while the crude oil composition of the non-wetting phase fluid remains constant.

It is important to note that the test cell(s) of the present application measure interfacial tension between the non-wetting phase fluid and the wetting phase fluid of the slug flow based on non-optical technique, and thus are particularly suitable for high pressure and high temperature environments, such as downhole applications in a wellbore for wireline testing application, or as a remote sensor in an observation well for enhanced oil recovery (EOR) monitoring. This instrument is especially suitable to screen the impact of surfactants on the oil-water interfacial tension. The test cell is especially suited for high pressure or downhole applications because of the pressure difference measuring principle used. Practically, the whole test cell and pressure sensor can be put into the high-pressure environment. Note that the electronics of the pressure sensor can be housed in a pressure and temperature controlled environment of the downhole tool if the pressure sensor utilizes pressure and temperature electronic components. For instance, a differential pressure sensor based on membrane movement would not be affected by the absolute hydrostatic pressure. However, the high temperature might have an effect on the sensitivity of the differential pressure sensor. For such cases, the pressure sensor can be kept at a constant temperature within the high pressure chamber. This results in a temperature gradient along the connection tubing between the high temperature capillary cell and the controlled temperature pressure sensor, but should not result in any appreciable pressure difference, which would be an artifact. If, however, a temperature-induced phase change can be expected in the measured wetting phase (which is situated in the connection tubing between the pressure sensor and the capillary cell), it is advisable to have a perfectly symmetrical pair of connection tubes, which are bound together, so the lengths of the condensed phase (if there is any) are identical in both the connection tubes of the pressure sensor. Therefore, the hydrostatic pressures of the condensed phase parts are the same and would not alter the differential pressure. Alternatively, the connection tubes can be filled up with a fluid, which would not have phase changes within the operational pressure and temperature window and would not mix with the measured phases. Yet another option is to use not a single differential sensor but two absolute pressure sensors to measure the pressure differences. In this case, the connection tubes and the issues with the phase changes in them can be avoided. The proper sized slugs can be generated by using miniature displacement pumps, one for each of the phases, which are connected to connector tube 13 on FIG. 1. The slugs can be generated by activating the movement of the displacement pistons alternately. This assumes that the produced oil and water phases are collected separately or they are already separated. This separation can be done either in a miniature centrifuge or with a membrane separation process. However, this separation is not absolutely needed when the oil-water or gas-liquid sample from the reservoir is collected into chamber 11 on FIG. 1. In this latter chamber, a two-phase system (for instance an emulsion) can be established and the approximate drop size ensured by stirring. To operate this device it is not necessary to fully control the size of the slugs. The size of the slugs can form a wide distribution. For this case, the measured differential pressure functions can be filtered and those differential pressures shapes can be rejected which would not correspond to the ideal arrangement described in FIGS. 3-5.

In the above parts, with the geometric construction of the cell and with the applied limitations (based on the Eotvos number and perfect wetting conditions), the shapes of the menisci are controlled, which makes possible utilization of the simple mathematical formulas of Equations (3), (5), (6), and (8) for the calculation of the interfacial tension from the differential pressure data. If the cell geometry is not as above, spherical meniscus shapes cannot be assumed. For instance, the cross section of the Venturi arrangement (which was cylindrical in all the above sections) can be changed to rectangular or possibly to polygonal. For these cases, the differential pressure through the meniscus will be dependent on the curvature of the meniscus; however, the mathematical expression of this differential pressure may be very complicated due to the complicated meniscus shape. For such complicated geometries, analytical expression of the interfacial tension as a function of the pressure difference might not even be found. For these cases, the relationship between the differential pressure and interfacial tension can be replaced by a correlation between the interfacial tension and differential pressure. Such correlation can be established by calibrating the selected cell, which does not necessarily have cylindrical symmetry and can have elliptical or polygonal (including rectangular) cross sections, or the cell may have a curve-polygon cross section (in which some or all sides of the polygon are replaced with curves). The only requirement for this altered cell is a geometry in which the curvature of the meniscus is dependent on the position of the meniscus in the flow-through cell. This results in a differential pressure, which is dependent on the position of the meniscus. For this configuration, it is still important to measure the pressure difference between upstream and downstream points of the same phase to eliminate some zero point issues of the differential pressure sensor. A preferable configuration is similar to that shown in FIG. 5, i.e. a device that consists of a tube of constant cross-section, narrowing part, and another tube of constant cross-section that is smaller than the cross-section of the first tube. No restrictions are imposed on cross-sectional shapes of these three parts of the device. The parts may also be non-coaxial. Consequently, slugs injected into this more broadly defined cell must be long enough such that during their displacement they occupy simultaneously the middle narrowing part and both the wider and the narrow tubes during a time period sufficient to obtain an accurate pressure difference dependence on droplet displacement. During this time period, the pressure difference will be nearly constant and is dictated by the dimensions of both the tube cross-sections. The deviations from constant pressure difference will mainly be caused by channel imperfections caused by manufacturing. Calibration is performed with a set of liquids with known interfacial tensions. The slug injection experiments are performed with these calibrating solutions and the interfacial tension versus differential pressure correlation is populated with experimental points. This correlation curve can be used for determining the interfacial tension of unknown fluid by measuring the differential pressure when a slug is injected and reading the interfacial tension from the established correlation.

There have been described and illustrated herein several embodiments of an apparatus and method that characterizes interfacial tension between two immiscible or partially miscible fluids. It will therefore be appreciated by those skilled in the art that yet other modifications could be made to the provided invention without deviating from its scope as claimed.

What is claimed is:

1. An apparatus for characterizing interfacial tension between a non-wetting phase fluid and a wetting phase fluid of a slug flow, comprising:
   a capillary structure configured to contain a slug of the non-wetting phase fluid of the slug flow, the slug having a leading edge meniscus and a trailing edge meniscus, and the capillary structure having a venturi-like section;
   a pressure sensor configured to measure differential pressure between first and second locations of the capillary structure, the first location disposed upstream of the leading edge meniscus of the slug with the leading edge meniscus of the slug contained within the venturi-like section of the capillary structure, and the second location disposed downstream of the trailing edge meniscus of the slug; and
   data processing means, operably coupled to the pressure sensor, for deriving a measure of interfacial tension between the non-wetting phase fluid and the wetting phase fluid of the slug flow based upon the differential pressure measured by the pressure sensor.

2. An apparatus according to claim 1, wherein the data processing means derives the measure of interfacial tension between the non-wetting phase fluid and the wetting phase fluid of the slug flow based further on geometry of the capillary structure.

3. An apparatus according to claim 1, wherein the data processing means derives the measure of interfacial tension between the non-wetting phase fluid and the wetting phase fluid of the slug flow based further on calibration of the apparatus.

4. An apparatus according to claim 1, wherein:
   the pressure sensor is adapted to measure a static differential pressure between the first and second locations of the capillary structure; and
   the data processing means derives the measure of interfacial tension between the non-wetting phase fluid and the wetting phase fluid of the slug flow based on the static differential pressure measured by the pressure sensor.

5. An apparatus according to claim 1, wherein:
   the pressure sensor is adapted to measure a plurality of dynamic differential pressures between the first and second locations of the capillary structure at different flow rates of the slug flow;
   the data processing means is adapted to derive static differential pressure between the first and second locations of the capillary structure based upon the plurality of dynamic differential pressures measured by the pressure sensor; and
   the data processing means derives the measure of interfacial tension between the non-wetting phase fluid and the wetting phase fluid of the slug flow based on the static differential pressure derived by the data processing means.

6. An apparatus according to claim 1, wherein the capillary structure is configured to allow for flow of the slug flow through the capillary structure.

7. An apparatus according to claim 1, wherein the capillary structure comprises three co-axial cylindrical sections including an intermediate cylindrical section disposed between two outer cylindrical sections, the two outer cylindrical sections having a larger diameter than the intermediate cylindrical section, wherein the intermediate cylindrical section is the venturi-like section.

8. An apparatus according to claim 7, wherein the capillary structure is oriented such that the three co-axial cylindrical sections extend in a horizontal direction.

9. An apparatus according to claim 7, wherein the capillary structure is oriented such that the three co-axial cylindrical sections extend in a vertical direction.

10. An apparatus according to claim 7, wherein:
    the measure of interfacial tension between the non-wetting phase fluid and the wetting phase fluid of the slug flow is calculated by the data processing means according to the following equation:

$$\Delta P = 2\gamma \left( \frac{1}{R_{P1}} - \frac{1}{R_{P2}} \right),$$

where $\gamma$ is the measure of interfacial tension between the non-wetting phase fluid and the wetting phase fluid of the slug flow,
$\Delta P$ is a static differential pressure between the first and second locations of the capillary structure,
$R_{P1}$ is the radius of the intermediate cylindrical section of the capillary structure, and
$R_{P2}$ is the radius of the outer cylindrical sections of the capillary structure.

11. An apparatus according to claim 7, wherein:
    the measure of interfacial tension between the non-wetting phase fluid and the wetting phase fluid of the slug flow is calculated by the data processing means according to the following equation:

$$\Delta P = \frac{2\gamma}{R_{P1}},$$

where $\gamma$ is the measure of interfacial tension between the non-wetting phase fluid and the wetting phase fluid of the slug flow,
$\Delta P$ is a static differential pressure between the first and second locations of the capillary structure, and
$R_{P1}$ is the radius of the intermediate cylindrical section of the capillary structure.

12. An apparatus according to claim 9, wherein:
    the measure of interfacial tension between the non-wetting phase fluid and the wetting phase fluid of the slug flow is calculated by the data processing means according to the following equation:

$$\Delta P = \frac{2\gamma}{R_{P1}} - g\left[ L_2 \rho_{wetting} + (L_1 - L_2)\rho_{non\text{-}wetting} + (L_3 - L_1)\rho_{wetting} \right],$$

where $\gamma$ is the measure of interfacial tension between the non-wetting phase fluid and the wetting phase fluid of the slug flow,
$\Delta P$ is a static differential pressure between the first and second locations of the capillary structure;
$R_{P1}$ is the radius of the intermediate cylindrical section of the capillary structure,
$L_1$ is a distance between the first location and the leading edge meniscus of the slug during the measurement of the static differential pressure $\Delta P$,
$L_2$ is a distance between the first location and the trailing edge meniscus of the slug during the measurement of the static differential pressure $\Delta P$, $L_3$ is the distance between the first location and the second location, $\rho_{wetting}$ is the density of the wetting phase fluid of the slug flow, and $\rho_{non-wetting}$ is the density of the non-wetting phase fluid of the slug flow.

13. An apparatus according to claim 1, wherein the venturi-like section of the capillary structure has a tapered conical form.

14. An apparatus according to claim 13, wherein:
the measure of interfacial tension between the non-wetting phase fluid and the wetting phase fluid of the slug flow is calculated by the data processing means according to the following equation:

$$\Delta p_{12} = 2\gamma \left( \frac{1}{R_1} - \frac{1}{R_2} \right),$$

where $\gamma$ is the measure of interfacial tension between the non-wetting phase fluid and the wetting phase fluid of the slug flow, $\Delta p_{12}$ is a differential pressure between the first and second locations of the conical form venturi-like section of the capillary structure, $R_1$ is the radius of the leading edge meniscus of the slug contained in the venturi-like section of the capillary structure during the measurement of the differential pressure $\Delta p_{12}$, $R_2$ is the radius of the trailing edge meniscus of the slug contained in the venturi-like section of the capillary structure during the measurement of the differential pressure $\Delta p_{12}$, $R_1$ and $R_2$ are related by a mathematical model of droplet motion in the capillary structure, and the differential pressure $\Delta p_{12}$ is related to the measure of interfacial tension $\gamma$ by a parametric function.

15. A method for characterizing interfacial tension between a non-wetting phase fluid and a wetting phase fluid of a slug flow, comprising:
containing a slug of the non-wetting phase fluid of the slug flow in a capillary structure, the slug having a leading edge meniscus and a trailing edge meniscus, and the capillary structure having a venturi-like section;
measuring differential pressure between first and second locations of the capillary structure, the first location disposed upstream of the leading edge meniscus of the slug with the leading edge meniscus of the slug contained within the venturi-like section of the capillary structure, and the second location disposed downstream of the trailing edge meniscus of the slug; and
deriving a measure of interfacial tension between the non-wetting phase fluid and the wetting phase fluid of the slug flow based upon the measured differential pressure.

16. A method according to claim 15, wherein the measure of interfacial tension between the non-wetting phase fluid and the wetting phase fluid of the slug flow is based further on geometry of the capillary structure.

17. A method according to claim 15, wherein the measure of interfacial tension between the non-wetting phase fluid and the wetting phase fluid of the slug flow is based further on calibration of the apparatus.

18. A method according to claim 15, wherein the measured differential pressure between the first and second locations of the capillary structure is a static differential pressure between the first and second locations of the capillary structure.

19. A method according to claim 15, further comprising:
measuring a plurality of dynamic differential pressures between the first and second locations of the capillary structure at different flow rates of the slug flow;
deriving static differential pressure between the first and second locations of the capillary structure based upon the plurality of dynamic differential pressures measured by the pressure sensor; and
deriving the measure of interfacial tension between the non-wetting phase fluid and the wetting phase fluid of the slug flow based on the derived static differential pressure.

20. A method according to claim 15, wherein the capillary structure is configured to allow for flow of the slug flow through the capillary structure.

21. A method according to claim 15, wherein the capillary structure comprises three co-axial cylindrical sections including an intermediate cylindrical section disposed between two outer cylindrical sections, the two outer cylindrical sections having a larger diameter than the intermediate cylindrical section, wherein the intermediate cylindrical section is the venturi-like section.

22. A method according to claim 21, wherein the capillary structure is oriented such that the three co-axial cylindrical sections extend in a horizontal direction.

23. A method according to claim 21, wherein the capillary structure is oriented such that the three co-axial cylindrical sections extend in a vertical direction.

24. A method according to claim 21, wherein:
the measure of interfacial tension between the non-wetting phase fluid and the wetting phase fluid of the slug flow is calculated according to the following equation:

$$\Delta P = 2\gamma \left( \frac{1}{R_{P1}} - \frac{1}{R_{P2}} \right),$$

where $\gamma$ is the measure of interfacial tension between the non-wetting phase fluid and the wetting phase fluid of the slug flow, $\Delta P$ is a static differential pressure between the first and second locations of the capillary structure, $R_{P1}$ is the radius of the intermediate cylindrical section of the capillary structure, and $R_{P2}$ is the radius of the outer cylindrical sections of the capillary structure.

25. A method according to claim 21, wherein:
the measure of interfacial tension between the non-wetting phase fluid and the wetting phase fluid of the slug flow is calculated according to the following equation:

$$\Delta P = \frac{2\gamma}{R_{P1}},$$

where $\gamma$ is the measure of interfacial tension between the non-wetting phase fluid and the wetting phase fluid of the slug flow, $\Delta P$ is a static differential pressure between the first and second locations of the capillary structure, and $R_{P1}$ is the radius of the intermediate cylindrical section of the capillary structure.

26. A method according to claim 23, wherein:

the measure of interfacial tension between the non-wetting phase fluid and the wetting phase fluid of the slug flow is calculated according to the following equation:

$$\Delta P = \frac{2\gamma}{R_{P1}} - g\left[L_2 \rho_{wetting} + (L_1 - L_2)\rho_{non\text{-}wetting} + (L_3 - L_1)\rho_{wetting}\right],$$

where $\gamma$ is the measure of interfacial tension between the non-wetting phase fluid and the wetting phase fluid of the slug flow, $\Delta P$ is a static differential pressure between the first and second locations of the capillary structure, $R_{P1}$ is the radius of the intermediate cylindrical section of the capillary structure, $L_1$ is a distance between the first location and the leading edge meniscus of the slug during the measurement of the static differential pressure $\Delta P$, $L_2$ is a distance between the first location and the trailing edge meniscus of the slug during the measurement of the static differential pressure $\Delta P$, $L_3$ is the distance between the first location and the second location, $\rho_{wetting}$ is the density of the wetting phase fluid of the slug flow, and $\rho_{non\text{-}wetting}$ is the density of the non-wetting phase fluid of the slug flow.

27. A method according to claim 15, wherein the venturi-like section of the capillary structure has a tapered conical form.

28. A method according to claim 27, wherein:

the measure of interfacial tension between the non-wetting phase fluid and the wetting phase fluid of the slug flow is calculated according to the following equation:

$$\Delta p_{12} = 2\gamma \left(\frac{1}{R_1} - \frac{1}{R_2}\right),$$

where $\gamma$ is the measure of interfacial tension between the non-wetting phase fluid and the wetting phase fluid of the slug flow, $\Delta p_{12}$ is a differential pressure between the first and second locations of the conical form venturi-like section of the capillary structure, $R_1$ is the radius of the leading edge meniscus of the slug contained in the venturi-like section of the capillary structure during the measurement of the differential pressure $\Delta p_{12}$, $R_2$ is the radius of the trailing edge meniscus of the slug contained in the venturi-like section of the capillary structure during the measurement of the differential pressure $\Delta p_{12}$, $R_1$ and $R_2$ are related by a mathematical model of droplet motion in the capillary structure, and the differential pressure $\Delta p_{12}$ is related to the measure of interfacial tension $\gamma$ by a parametric function.

* * * * *